US007179851B2

(12) United States Patent
Qin et al.

(10) Patent No.: US 7,179,851 B2
(45) Date of Patent: Feb. 20, 2007

(54) DAMAGE-RESISTANT SUPERABSORBENT MATERIALS

(75) Inventors: Jian Qin, Appleton, WI (US); Kenneth R. Schueler, Jr., Appleton, WI (US); Hoa La Wilhelm, Appleton, WI (US); Dave Allen Soerens, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 324 days.

(21) Appl. No.: 10/655,940

(22) Filed: Sep. 5, 2003

(65) Prior Publication Data
US 2005/0054784 A1 Mar. 10, 2005

(51) Int. Cl.
*A61L 15/60* (2006.01)

(52) U.S. Cl. ............... 523/200; 524/457; 524/502; 525/185; 428/542

(58) Field of Classification Search ........ 428/542; 252/8.61; 524/500, 457, 502; 523/200; 525/185
See application file for complete search history.

(56) References Cited

U.S. PATENT DOCUMENTS

| 6,323,252 B1* | 11/2001 | Gartner et al. ............... 521/149 |
| 6,387,495 B1 | 5/2002 | Reeves et al. |
| 6,391,451 B1* | 5/2002 | Mitchell et al. ............. 428/402 |
| 6,414,214 B1* | 7/2002 | Engelhardt et al. ......... 604/368 |
| 6,596,402 B2 | 7/2003 | Soerens et al. |
| 2002/0150761 A1 | 10/2002 | Lange et al. |
| 2004/0071966 A1* | 4/2004 | Inger et al. .................. 428/394 |
| 2005/0027268 A1* | 2/2005 | Qin et al. .................... 604/367 |
| 2005/0245393 A1* | 11/2005 | Herfert et al. ............... 502/402 |

FOREIGN PATENT DOCUMENTS

WO   WO 01/66056 A1   9/2001

* cited by examiner

*Primary Examiner*—Kelechi C. Egwim
(74) *Attorney, Agent, or Firm*—Pauley Petersen & Erickson

(57) ABSTRACT

Superabsorbent material treated to resist damage when subjected to an Absorbent Product Processing Simulation Test, which simulates the mechanical damage that occurs during current commercial diaper manufacturing processes. The treated superabsorbent material has a centrifuge retention capacity of about 15 grams or greater of 0.9 weight percent sodium chloride per gram of the superabsorbent material and a gel bed permeability (GBP) at 0 psi swell pressure on pre-screened particles of about 200 ($\times 10^{-9}$ cm$^2$) or greater. After subjecting the treated superabsorbent material to the Absorbent Product Processing Simulation Test, the treated superabsorbent may exhibit minimal reduction in GBP of pre-screened or un-screened particles at 0 psi or at 0.3 psi swell pressure, as well as possibly exhibiting minimal reduction in average particle size diameter (PSD). The superabsorbent material can be treated by adding an aqueous solution of a hydrophilic soft polymer to the superabsorbent material, mixing the superabsorbent material with the aqueous solution, and drying the superabsorbent material.

28 Claims, 2 Drawing Sheets

DAMAGE-RESISTANT SUPERABSORBENT MATERIALS

BACKGROUND OF THE INVENTION

This invention is directed to superabsorbent materials that can withstand mechanical forces without a significant reduction in absorbency properties, specifically gel bed permeability and/or average particle size. This invention is also directed to methods of increasing the damage resistance of superabsorbent materials.

Commercial superabsorbent materials are widely used in a variety of personal care products, such as infant diapers, child training pants, adult incontinence products, feminine care products, and the like. These superabsorbent materials, or hydrogels, are essentially crosslinked polyelectrolytes, which are water-swellable, water-insoluble and exhibit very high water absorbency. In general, these crosslinked polyelectrolytes have a centrifuge retention capacity (CRC) of at least 15 grams of 0.9 weight percent sodium chloride aqueous solution per gram of the polymer. Superabsorbent materials are also designed to quickly uptake bodily fluids, which requires that the superabsorbent materials have high gel bed permeability (GBP). Commercial superabsorbent materials undergo significant particle damage during manufacturing and converting processes, resulting in great loss of their original gel bed permeability. This reduction in the original gel bed permeability may be one of the causes of premature leakage and skin wetness problems.

These superabsorbent materials are characterized as glassy polymers and are very brittle under mechanical impact and stress when they are dry or at a low relative humidity (RH) environment, such as a RH below 30%. Due to their glassy and brittle nature, these polymers suffer a significant breakdown in particle size and shape during manufacturing processes, such as diaper manufacturing processes. Major mechanical damage of the polymers occurs from high-speed impact in air conveying and mixing steps and high-pressure compression in product densification steps. This particle damage is further increased in products employing high superabsorbent material content as product manufacturers strive for thinner products. This mechanically-induced damage to the superabsorbent materials reduces the effectiveness of the materials, also illustrated in the Examples herein.

There is thus a need or desire for a superabsorbent material that can withstand absorbent product manufacturing and converting processes without resulting in a significant reduction in absorbent properties, specifically gel bed permeability and/or particle size. There is a further need or desire for a method of increasing the damage resistance of a superabsorbent material.

SUMMARY OF THE INVENTION

This invention is directed to superabsorbent materials having improved resistance to mechanical damage and minimal loss of absorbent properties due to such damage compared to current commercially available superabsorbent materials, and methods of increasing the damage resistance and functional loss resistance of a superabsorbent material.

The superabsorbent materials of the invention after damage resistance treatment suitably have a centrifugal retention capacity of about 15 grams or greater of 0.9 weight percent sodium chloride aqueous solution per gram of the superabsorbent material, and a gel bed permeability (GBP) value at a 0 psi swell pressure measured on 300–600 micron particles of about 200 ($\times 10^{-9}$ cm$^2$) or greater, or about 300 ($\times 10^{-9}$ cm$^2$) or greater, or about 500 ($\times 10^{-9}$ cm$^2$) or greater, or about 800 ($\times 10^{-9}$ cm$^2$) or greater, and at least one the following properties: (1) a reduction in GBP value at a 0 psi swell pressure measured on 300–600 micron particles of about 20% or less following the herein described Absorbent Product Processing Simulation Test; (2) a reduction in GBP value at a 0.3 psi swell pressure measured on 300–600 micron particles of about 50% or less following the Absorbent Product Processing Simulation Test; (3) a reduction in GBP value at a 0 psi swell pressure measured on as-is particles of about 50% or less following the Absorbent Product Processing Simulation Test; (4) a reduction in GBP value at a 0.3 psi swell pressure measured on as-is particles of about 60% or less following the Absorbent Product Processing Simulation Test; and/or (5) an average particle size reduction measured on as-is particles of about 20% or less following the Absorbent Product Processing Simulation Test. The Absorbent Product Processing Simulation Test simulates the mechanical damage inflicted on superabsorbent material during current commercial diaper manufacturing processes.

The superabsorbent material can be treated with a non-particulate solution to increase the damage resistance of the material. For example, one method of treating the superabsorbent material to increase damage resistance of the material involves adding to the superabsorbent material an aqueous solution of a hydrophilic soft polymer which can be crosslinked to form a water-swellable but water-insoluble polymer, mixing the aqueous solution and the superabsorbent material, and drying the treated superabsorbent material. The hydrophilic soft polymer suitably has a glass transition temperature below about 20 degrees Celsius, and is suitably present in the aqueous solution in an amount between about 0.1% and about 10% by weight of the aqueous solution. The superabsorbent material may be treated with 10% to about 1000% aqueous solution by weight of the superabsorbent material.

The superabsorbent material, prior to treatment, may be a standard, commercially available, crosslinked polyelectrolyte, including anionic polymers, cationic polymers, or combinations thereof. The superabsorbent material may be biodegradable or non-biodegradable. The superabsorbent materials can include particles, fibers, tows, flakes, films, foams, and the like.

The superabsorbent materials of the invention, including the superabsorbent materials resulting from the methods of the invention, may be incorporated into any suitable absorbent article. Examples of such absorbent articles include, but are not limited to, infant diapers, child training pants, adult incontinence products, feminine care products, paper towels, tissues, and the like.

With the foregoing in mind, it is a feature and advantage of the invention to provide damage-resistant superabsorbent materials, and methods of increasing damage resistance of superabsorbent materials.

DEFINITIONS

Figure 1:
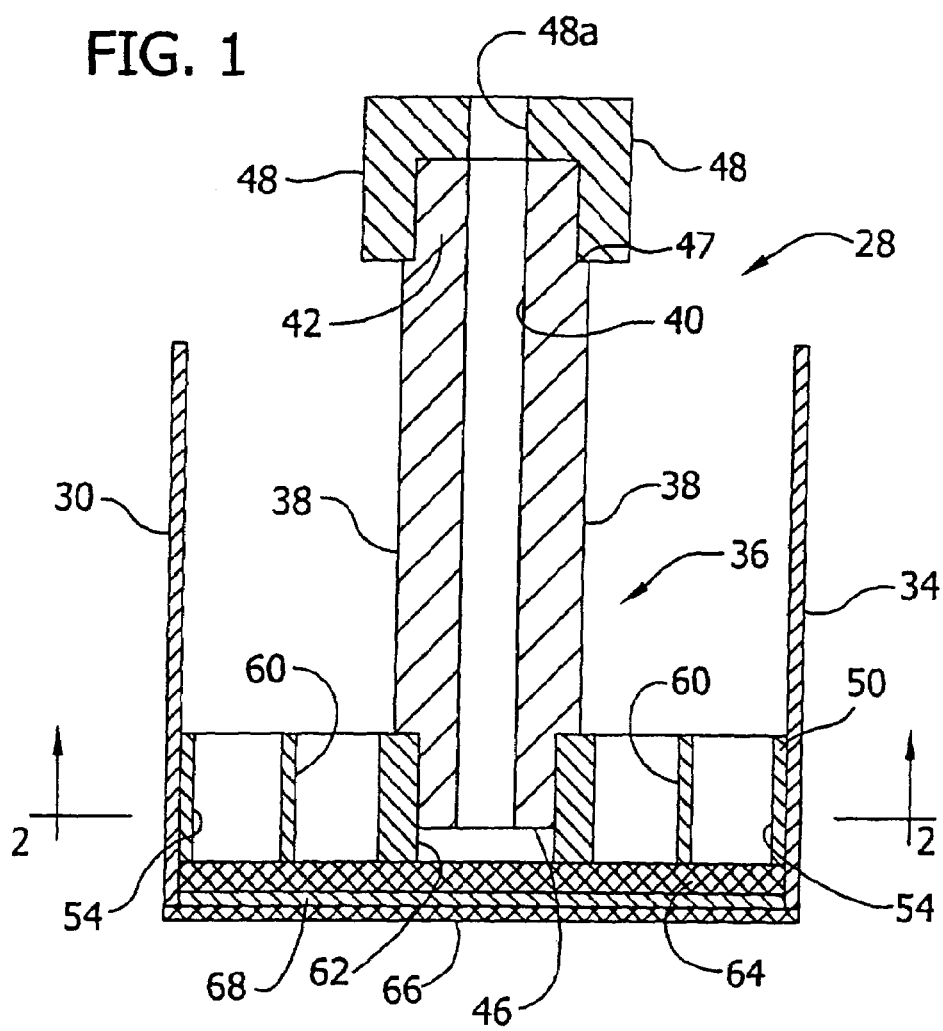
FIG. 1 depicts apparatus used to measure permeability of free-flowing particles.

Within the context of this specification, each term or phrase below will include the following meaning or meanings.

The term "superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The superabsorbent material may be biodegradable or non-biodegradable. The superabsorbent materials can include particles, fibers, tows, flakes, films, foams, and the like. A material is "absorbent" if it absorbs at least five times its weight of the aqueous solution under these conditions.

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "pre-screened," as used herein, refers to a sample of superabsorbent material that has been screened or otherwise sorted to include particles within a specified size range. Unless otherwise stated herein, the pre-screened superabsorbent materials include particles in a size ranging from 300 to 600 microns. A more detailed description of the screening process is provided below in the Average Particle Size Distribution Test Method.

The term "un-screened," as used herein, is used interchangeably with the term "as-is." These terms refer to a sample of superabsorbent material that has not been screened or otherwise sorted to include only particles within a specified size range. Instead, un-screened superabsorbent material may include particles of any size, such as particles that have undergone changes in size and shape as a result of mechanical damage.

The term "absorbent article" includes personal care absorbent articles such as diapers, training pants, swim wear, absorbent underpants, adult incontinence products, feminine hygiene products, and the like, as well as absorbent wiping articles such as facial tissue, paper towels, kitchen towels, away-from-home towels, wet-wipes, and the like, as well as medical absorbent articles such as medical absorbent garments, drapes, gowns, bandages, masks, wound dressings, underpads, wipes, and the like.

The term "hydrophilic" refers to a material having a contact angle of water in air of less than 90 degrees. For purposes of this application, contact angle measurements are determined as set forth in "Surface and Colloid Science—Experimental Methods," Vol. II, Robert J. Good and Robert J. Stromberg, Ed. (Plenum Press, 1979).

The term "hydrophilic soft polymer" refers to a material that results from the polymerization of water-soluble monomers with alkyl chains of 3 carbons or less, and having a glass transition temperature (Tg) of less than 20 degrees Celsius for the dried polymer. Hydrophilic soft polymers act as an elastomer at room temperature and are capable of rapid, nonradiative crosslinking.

The term "non-particulate solution" refers to a homogeneous mixture of two or more substances, which may be solids, liquids, gases, or a combination of these, wherein the solution does not include non-dissolved solid particles therein.

These terms may be defined with additional language in the remaining portions of the specification.

DESCRIPTION OF PREFERRED EMBODIMENTS

In accordance with the invention, damage-resistant superabsorbent materials can be achieved using the methods described herein. These superabsorbent materials have improved resistance to mechanical damage, particularly damage resulting from absorbent product processing, and reduced functional loss compared to current commercially available superabsorbent materials.

The superabsorbent materials of the invention include conventional superabsorbent material that has been treated to resist damage when subjected to an Absorbent Product Processing Simulation Test, described in detail in the Examples below. Conventional superabsorbent materials are crosslinked polyelectrolytes. Polyelectrolytes include both anionic and cationic polymers. Anionic polymers contain functional groups such as carboxyl, sulfonate, sulphate, sulfite, phosphate, or a mixture thereof. Examples of anionic polymers include, but are not limited to, salts or partial salts of polyacrylic acid, polyacrylamido methylpropane sulfonic acid, polyvinyl acetic acid, polyvinyl phosphonic acid, polyvinyl sulfonic acid, isobutylene-maleic anhydride copolymer, carboxymethyl cellulose, alginic acid, carrageenan, polyaspartic acid, polyglutamic acid, and copolymers or mixtures thereof. Cationic polymers contain functional groups such as primary, secondary, and tertiary amine, imine, amide, quaternary ammonium, or mixtures thereof. Examples of cationic polymers include, but are not limited to, salts or partial salts of polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine, and copolymers or mixtures thereof. Examples of commercially available superabsorbent materials include SXM 9543 and FAVOR 880, both available from Stockhausen Inc. in Greensboro, N.C., U.S.A., and Dow DRYTECH 2035, available from Dow Chemical Co. in Midland, Mich., U.S.A. These and other superabsorbent materials, including multicomponent superabsorbent material (i.e., superabsorbents with both anionic and cationic polymers) and biodegradable superabsorbents, are suitable for use in the invention.

Like conventional superabsorbent materials, the treated superabsorbent materials of the invention exhibit a centrifuge retention capacity (CRC) of at least 15 grams of 0.9 weight percent sodium chloride aqueous solution per gram of the polymer or superabsorbent and a gel bed permeability (GBP) value at a 0 psi swell pressure measured on 300–600 micron particles of at least about 200 ($\times 10^{-9}$ cm$^2$), or at least 300 ($\times 10^{-9}$ cm$^2$), or at least 500 ($\times 10^{-9}$ cm$^2$), or at least 800 ($\times 10^{-9}$ cm$^2$). Alternatively, the treated superabsorbent materials of the invention may exhibit a CRC of about 20 grams or greater, or about 25 grams or greater of 0.9 weight percent sodium chloride aqueous solution per gram of the superabsorbent material prior to undergoing an absorbent structure, material, or article manufacturing process. However, the treated superabsorbent materials of the invention are not as brittle as conventional superabsorbent materials and, therefore, incur less damage during absorbent article manufacturing processes, as illustrated in the Examples below.

Damage resistance of the superabsorbent material can be increased by treating the superabsorbent material with a non-particulate solution. For example, one method of treating superabsorbent material to increase damage resistance of the material involves the use of additives to surface treat the superabsorbent materials, as described in Example 5 below. In this approach, suitable additives are hydrophilic soft polymers having a glass transition temperature (Tg) at about 20 degrees Celsius or less, or about 10 degrees Celsius or less, or about 0 degree Celsius or less. The lower the Tg, the softer a polymer is. Examples of suitable hydrophilic soft polymers include hydroxypropyl cellulose, polyethylene oxide, polypropylene oxide, polyethylene glycol, polypropylene glycol, and hydrophilic acrylate or methacrylate copolymers, including polyethylene glycol-grafted copolymers. The hydrophilic soft polymer is suitably in an aqueous solution, present in an amount between about 0.1% and about 10%, or between about 0.5% and about 8%, or between about 2% and about 5% by weight of the aqueous solution. The aqueous solution can be added to the superabsorbent material in an amount between about 10% and about 1000%, or between about 50% and about 800%, or between about 100% and about 500% by weight of the superabsorbent material. The aqueous solution and the superabsorbent material are then mixed together. To ensure a uniform surface coating, the mixture of aqueous solution and superabsorbent material can be stirred for about 0.1 to about 10 minutes. After the aqueous solution has been added to the superabsorbent material, the superabsorbent material can be dried, suitably at a temperature between about 20 and about 150, or between about 50 and about 100 degrees Celsius, for a period of about 0.1 to about 30 hours, or about 1 to about 10 hours. The dried superabsorbent material including the additive can be screened through a sieve, and any agglomerated particles can then be separated. The agglomerated particles can be pressed by hand or by using equipment capable of providing gentle pressing and kneading to avoid undue damage to the particles.

The hydrophilic soft polymers disclosed by this application can be crosslinked to form water-swellable but water-insoluble polymers to provide additional absorbency. Furthermore, the hydrophilic soft polymers can significantly increase GBP values of the treated superabsorbents. Uniform coating may be achieved by crosslinking the hydrophilic soft polymers after they have been coated onto the superabsorbent materials. There are two mechanisms to achieve crosslinking after the surface treatment. One mechanism is to use a latent crosslinking agent, and the other is to use a modified hydrophilic soft polymer which is self-crosslinkable. A latent crosslinking agent does not react with the hydrophilic soft polymer in the aqueous solution or during surface treatment. It only reacts with the polymer when a proper condition is provided after the polymer has been dried. Such proper conditions include heating, microwave treatment, electron-beam radiation, UV, high humidity, and organic solvent treatment, for example. Suitable latent crosslinkers include, but are not limited to, any organic compounds having at least two functional groups or functionalities capable of reacting with pendant groups on the hydrophilic soft polymer, such as hydroxyl groups, amino groups, carboxylic acid groups, carboxyl groups, imino groups, glycol groups, oxide groups, epoxy groups, isocynate groups, aziridino groups, and combinations thereof Examples include butanediol, ethylene glycol, diethylene triamine, citric acid, sodium tricitrate, polyethylene oxide, polyvinyl amine, polyvinyl alcohol, polyacrylic acid, polyethylene imine, polyethylene glycol, glycerol polyglycidyl ether, epichlorohydrin, polyisocyanate, polyaziridine compounds, polyvinyl amine, polyquaternary amines, hydroxypropyl cellulose, methyl cellulose, starch, carboxymethyl cellulose, chitosan, chitosan salt, alginic acid, carregeena, polyaspartic acid, polylysin, polysuccinic acid, polyglutamic, acid, and mixtures of any of these. Other suitable latent crosslinkers include cations or anions having a valence of at least three, such as $Al^{3+}$, $Fe^{3+}$, $Zr^{4+}$, $Ti^{3+}$, $Co^{3+}$, $Fe^{4+}$, $Cr^{3+}$, $Ce^{3+}$, $Ce^{4+}$, $-PO_4^{3-}$, for example. Cations can be used as latent crosslinkers to crosslink a hydrophilic soft polymer having anionic pendant groups, while anions can be used to crosslink cationic pendant groups.

Self-crosslinkable latent crosslinkers include about 0.1 to about 20% by mass of acrylate or methacrylate ester units that include an alkoxysilane functionality. Upon exposure to water, the alkoxysilane functionality forms a silanol group which condenses to form a crosslinked polymer.

The hydrophilic soft polymer may also include about 0.1 to about 75% by mass of polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provides the hydrophilic soft polymer with enhanced flexibility. Thus, the hydrophilic soft polymer has enhanced adhesion in a wet condition, absorbency, and flexibility.

The hydrophilic soft polymer can be prepared using a template polymerization process by which the monoethylenically unsaturated polymer and acrylate or methacrylate ester are polymerized in the presence of a pre-formed template polymer, namely the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include, without limitation, ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting hydrophilic soft polymer may contain the polyolefin glycol and/or oxide as a separate component, or as part of the copolymer, or a combination of both.

The resulting polymer has latent moisture-induced crosslinking capability due to the alkoxysilane functionality. This polymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, hydrolysis of the alkoxysilane and subsequent condensation may occur after solvent removal by exposure of the coating to moisture in ambient air.

Yet another method of treating superabsorbent material to increase damage resistance of the material involves adding absorbent particulate material to the superabsorbent material. One example of a suitable absorbent particulate material includes, but is not limited to, crosslinked poly(ethylene oxide), as described in U.S. Pat. No. 6,596,402, issued to Soerens, et al., which is incorporated herein by reference in its entirety in a manner consistent with the present document.

The absorbent particulate material can be added to the superabsorbent material in an amount between about 0.5% and about 10%, or between about 1% and about 5%, or between about 2% and about 4% by weight of the superabsorbent material. The absorbent particulate material can be formed onto the superabsorbent material in the form of an aqueous or alcohol solution, or blends of water and a suitable alcohol, such as methanol or ethanol. Addition of the solution to superabsorbent material, followed by drying, results in the formation of discontinuous plaques of crosslinked, absorbent poly(ethylene oxide) particles, for example, on the surface of the superabsorbent material. All other aspects of this embodiment remain consistent with the previous embodiments.

All of these methods are capable of significantly reducing superabsorbent damage, as evidenced by the minimal reduction in gel bed permeability (GBP) of pre-screened or un-screened particles at 0 psi or at 0.3 psi swell pressure as well as the minimal reduction in average particle size diameter (PSD) of these materials following the Absorbent Product Processing Simulation Test. The Absorbent Product Processing Simulation Test was created to simulate the mechanical forces typically applied to superabsorbent materials during the manufacturing processes of absorbent articles. The development of this test is described in further detail in Examples 1 and 2 below. The Examples below further demonstrate the amount of damage that occurs to both commercial superabsorbent materials and the treated superabsorbent materials of the invention. More particularly, pre-screened (300–600 microns) damaged commercial superabsorbent materials typically have at least 30% reduction in GBP @ 0 psi and 60% reduction in GBP @ 0.3 psi. As-is damaged commercial superabsorbent materials have at least 50% reduction in GBP @ 0 psi and 95% reduction in GBP @ 0.3 psi, and at least 25% reduction in average particle size following the Absorbent Product Processing Simulation Test, compared to their virgin materials before being subjected to the simulation test. In contrast, the treated superabsorbent materials of the invention possess superior superabsorbent properties, as exhibited by a centrifuge retention capacity (CRC) of about 15 g/g or greater, or about 20 g/g or greater, or about 25 g/g or greater; a GBP @ 0 psi swell pressure measured on 300–600 micron particles of about 200 ($\times 10^{-9}$ cm$^2$) or greater, or about 300 ($\times 10^{-9}$ cm$^2$) or greater, or about 500 ($\times 10^{-9}$ cm$^2$) or greater, or about 800 ($\times 10^{-9}$ cm$^2$) or greater; and at least one of the following absorbent properties: (1) a reduction in GBP @ 0 psi on 300–600 micron particles of about 20% or less, or about 10% or less, or about 5% or less; (2) a reduction in GBP @ 0.3 psi on 300–600 micron particles of about 50% or less, or about 30% or less, or about 20% or less; (3) a reduction in GBP @ 0 psi on as-is particles of about 50% or less; (4) a reduction in GBP @ 0.3 psi on as-is particles of about 60% or less, or about 40% or less; and/or (5) average particle size reduction of about 20% or less, after the treated superabsorbent material is exposed to the Absorbent Product Processing Simulation Test. The treated superabsorbent materials of the invention may exhibit one, two, three, four, or all five of these absorbent properties.

The treatment methods of the invention can be carried out, wholly or in part, as part of the superabsorbent manufacturing process, or any other time prior to or subsequent to incorporating the superabsorbent material into an absorbent article, or even during the absorbent structure, material, or article manufacturing process.

The superabsorbent materials of the invention can be incorporated into, or formed into, any suitable absorbent structures and/or articles. Examples of suitable absorbent structures include, but are not limited to, homogeneous or heterogeneous mixtures of superabsorbent materials and fibers including natural and/or synthetic fibers, structures comprising layer(s) or discreet pockets of superabsorbent materials adjacent to layer(s) of fibers or nonwoven materials, foams, in-situ polymerization structures, and the like. Examples of suitable absorbent articles include, but are not limited to, personal care products such as diapers, training pants, swim wear, absorbent underpants, adult incontinence products, feminine hygiene products, and the like, as well as absorbent wiping articles such as facial tissue, paper towels, kitchen towels, away-from-home towels, wet-wipes, cleaning devices, and the like, as well as medical absorbent articles such as medical absorbent garments, drapes, gowns, bandages, masks, wound dressings, underpads, wipes, and the like. For example, the absorbent article may include an absorbent layer made up of, or including at least one region containing, at least about 10%, or at least about 40%, or at least about 60%, or at least about 80% by weight treated superabsorbent material, based on total weight of the absorbent layer. As used herein, the term "absorbent layer" refers to a component or structure that contains superabsorbent material. The absorbent layer may also include, fibers, natural or synthetic fibers, functional additives or surfactants, and the like. The absorbent layer may be wrapped within a tissue layer or other suitable wrap material, but for purposes of calculating the composition of the absorbent layer, the absorbent layer does not include the wrap layer.

EXAMPLES

Example 1

This Example illustrates the changes that occur in superabsorbent properties and average particle size of superabsorbent materials as a result of undergoing processing on a diaper production line. Table 1 summarizes these changes. The virgin materials are the materials in the condition in which they are received from the superabsorbent material manufacturer prior to being incorporated into an absorbent article. The reclaimed materials are the materials in the condition in which they are found after being incorporated into a commercially available absorbent article. The reclaimed superabsorbent materials were obtained using pulsing air turbulence and a rubber beater at a low or intermediate speed to separate superabsorbent from fluff in diaper absorbent cores.

The superabsorbents tested were virgin SXM 9543 from two different lots, available from Stockhausen Inc. in Greensboro, N.C., U.S.A.; and virgin Dow DRYTECH 2035, available from Dow Chemical Co. in Midland, Mich., U.S.A. The corresponding reclaimed superabsorbent materials were all obtained from commercial Huggies® diapers, available from Kimberly-Clark Corporation in Neenah, Wis., U.S.A.

TABLE 1

Absorbent Properties & Average PSD of Virgin and Reclaimed SAPs

| Property | SXM 9543[1] Virgin | SXM 9543[1] Reclaimed | Dow 2035[2] Virgin | Dow 2035[2] Reclaimed | SXM 9543[3] Virgin | SXM 9543[3] Reclaimed |
|---|---|---|---|---|---|---|
| CRC (g/g) | 21.8 | 23.3 | 28.5 | 29.0 | 22.5 | 23.7 |
| 0.9 AUL (g/g) | 20.1 | 20.0 | 13.6 | 14.5 | 19.9 | 19.1 |
| GBP @ 0 psi on 300–600 micron particles ($\times 10^{-9}$ cm$^2$) | 263 | 188 | 19 | 12 | 257 | 120 |
| Reduction in GBP @ 0 psi | | −28.5% | | −36.8% | | −53.3% |
| GBP @ 0.3 psi on 300–600 micron particles ($\times 10^{-9}$ cm$^2$) | 139 | 86 | 3 | 1 | 121 | 47 |
| Reduction in GBP @ 0.3 psi | | −38.1% | | −66.7% | | −61.2% |
| GBP @ 0 psi on as-is particles ($\times 10^{-9}$ cm$^2$) | 164 | 68 | 7 | 3 | 131 | 50 |
| Reduction in GBP @ 0 psi | | −58.5% | | −57.1% | | −61.8% |
| GBP @ 0.3 psi on as-is particles ($\times 10^{-9}$ cm$^2$) | 69 | 34 | 1 | 0 | 58 | 25 |
| Reduction in GBP @ 0.3 psi | | −50.7% | | −100% | | −56.9% |
| Average PSD (μm) | 356.4 | 259.5 | 330.1 | 248.9 | 367.1 | 238.7 |
| Reduction in average PSD | | −27.2% | | −24.6% | | −35.0% |

[1] lot #X202804004
[2] lot #PL08011Y70
[3] lot #G1L311AA

The data in Table 1 indicates that gel bed permeability, with or without swelling pressure, measured on pre-screened 300–600 micron particles or un-screened as-is particles, and average particle size of the superabsorbent materials are significantly reduced as a result of undergoing the diaper manufacturing process. Thus, it can be seen from this data that major mechanical damage and functional loss of the superabsorbent materials occurs in the diaper manufacturing process.

Example 2

In order to develop a bench method capable of mimicking the degree of damage inflicted on superabsorbent materials in commercial diaper lines, specifically the average PSD and its reduction, while simultaneously producing adequate sample sizes for making absorbent composites for small-scale diaper use testing, a commercial blender, OSTERIZER® 12-speed, available from Sunbeam Products, Inc., of Boca Raton, Fla., was used.

Fifty grams of as-is ("virgin") particulate superabsorbent received from vendors or later modified/treated as described herein was added into the blender each time and then the blender ran for a varied amount of time (15, 30, and 60 seconds) while the blender was set at a combination of "high speed" and "blend" settings. Length of blending time was used to correspond with damage level, with longer time representing more severe damage. Table 2 lists data to support this hypothesis. Also based on the data in Table 2, the 30-second blending method was selected to represent a level of damage similar to that of a commercial diaper manufacturing line. This method is referred to herein as the Absorbent Product Processing Simulation Test, and also described in the Test Methods section below.

Table 2 also compares damage inflicted on superabsorbent materials by a pilot line versus a commercial diaper line. The pilot line was used to make sample absorbent cores for evaluation. Reclaimed superabsorbent from these sample absorbent cores had a minimum reduction in average particle size compared to its virgin counterpart, which indicates that the pilot line inflicts minimum damage on superabsorbent due to slow production speed. This result also indicates that the reclaiming process has a minimum damage impact on superabsorbent material.

TABLE 2

PSD of Damaged SXM 9543

| Property | SXM 9543[3] Virgin | SXM 9543[3] Reclaimed from Pilot Line | SXM 9543[3] Reclaimed from Diaper | SXM 9543[3] @ Blending Time 15 seconds | SXM 9543[3] @ Blending Time 30 seconds | SXM 9543[3] @ Blending Time 60 seconds |
|---|---|---|---|---|---|---|
| Average PSD (μm) | 367.1 | 336.4 | 259.5 | 288.2 | 245.2 | 202.1 |
| Reduction in average PSD | | −8.4% | −29.3% | −21.5% | −33.2% | −44.9% |

Example 3

Three types of commercial superabsorbents, namely SXM 9543 and FAVOR 880, both available from Stockhausen Inc., and Dow DRYTECH 2035, available from Dow Chemical Co., were separately damaged by the 30-second blending method described in Example 2 and their properties were measured and listed in Table 3. All three commercial superabsorbents were damageable by mechanical impact and stress. The samples labeled as "Virgin" in Table 3 did not undergo the blending process. The samples labeled as "Blend" were blended for 30 seconds as described above. The samples with particle size of 300–600 microns exhibited reductions in GBP @ 0 psi of about 30% or greater and in GBP @ 0.3 psi of about 60% or greater, while as-is particles exhibited a loss in GBP @ 0 psi of about 50% or greater and GBP @ 0.3 psi of about 95% or greater, and average particle size reduction of about 25% or greater compared to their virgin superabsorbents.

posite material had approximately 600 gsm total basis weight and 0.22 g/cc density. The absorbent composite material was die-cut and assembled into absorbent cores for diaper testing. Each core contained 2 layers of the absorbent composite material, a bottom layer having the same T-shape as in a current commercial Step 4 HUGGIES® Ultratrim diaper core, and a top layer having a 2⅞ inch (7.3 cm) by 9 inch (22.9 cm) rectangular shape and set back 3.5 cm from a front edge of the bottom layer. Step 4 HUGGIES® Ultratrim diapers are available from Kimberly-Clark Corporation in Neenah, Wis. The surface area of the bottom layer was approximately 394 $cm^2$ and the surface area of the top layer was approximately 167 $cm^2$. The crotch width of the bottom layer was 3.5 inches (8.9 cm). The layers were adhesively laminated without tissue in between the layers. The layered absorbent cores were each then placed into a standard Step 4 HUGGIES® Ultratrim diaper chassis. This diaper modification was conducted by cutting out and removing the existing liner, surge, tissue, and absorbent pad

TABLE 3

GBP & PSD Values of Damaged Commercial Superabsorbents

| Property | SXM 9543[4] Virgin | SXM 9543[4] Damaged | Dow 2035[2] Virgin | Dow 2035[2] Damaged | FAVOR 880[5] Virgin | FAVOR 880[5] Damaged |
|---|---|---|---|---|---|---|
| CRC (g/g) | 21.2 | 22.5 | 28.5 | 29.4 | 30.9 | 32.2 |
| 0.9 AUL (g/g) | 20.1 | 19.5 | 13.6 | 9.9 | 22.2 | 16.1 |
| GBP @ 0 psi on 300–600 micron particles (×$10^{-9}$ $cm^2$) | 241.7 | 154.7 | 32 | 19 | 49.6 | 24.0 |
| Reduction in GBP @ 0 psi | | −36.0% | | −41.7% | | −51.6% |
| GBP @ 0.3 psi on 300–600 micron particles (×$10^{-9}$ $cm^2$) | 67.3 | 5.0 | 5 | 2 | 14.8 | 5.4 |
| Reduction in GBP @ 0.3 psi | | −92.6% | | −62.6% | | −63.5% |
| GBP @ 0 psi on as-is particles (×$10^{-9}$ $cm^2$) | 89 | 41 | 7.1 | 0.3 | 21 | 0.9 |
| Reduction in GBP @ 0 psi | | −53.9% | | −95.8% | | −95.7% |
| GBP @ 0.3 psi on as-is particles (×$10^{-9}$ $cm^2$) | 32 | 1.0 | 0.9 | 0 | 4.8 | 0.1 |
| Reduction in GBP @ 0.3 psi | | −96.9% | | −100% | | −97.9% |
| Average PSD (μm) | 357.2 | 257.9 | 330.1 | 205.2 | 314.2 | 219.7 |
| Reduction in average PSD | | −27.79% | | −37.82% | | −30.08% |

[4]lot #X210815
[5]lot #X106712B66

Example 4

Virgin and blended commercial superabsorbents SXM 9543 and Dow DRYTECH 2035 were incorporated into absorbent composites with wood pulp using the pilot line, which does minimum superabsorbent damage due to slow production speed.

The absorbent composite materials including virgin commercial superabsorbent are denoted as 0 second for damage level in Table 4, while composites including damaged or blended commercial superabsorbents are labeled to represent the degree of damage dependent upon how much blending time was applied.

Each absorbent composite material was prepared from approximately 45% superabsorbent and 55% wood pulp, available from Bowater, Coosa River, Ala., designated as CR 1654, by weight of the composite. The absorbent commaterials from standard Step 4 HUGGIES® Ultratrim diapers and replacing them with the new two-layered absorbent cores and new pieces of standard Step 4 HUGGIES® Ultratrim diaper liner, 2.5 osy surge, and tissue materials using lightly sprayed construction adhesive and adhesive tapes. The construction adhesive used was H2525A, which is a styrene block copolymer adhesive available from Findley Adhesives, Inc. of Wauwatosa, Wis.

The test involved 12 boys and 12 girls between the ages of 13 and 36 months with a weight range of 22 to 32 pounds and tested in both sitting and prone positions (on belly position). The subjects stayed in the sitting or prone position only during insult and an additional 30 seconds following the insult. Seventy (70) ml of 0.9 wt % sodium chloride aqueous solution were injected at a rate of 15 ml/sec into the diapers every 15 minutes until the garments leaked (when a first wet spot at least the size of a U.S.A. $0.25 coin (approximately 2.4 cm diameter) was observed on the cotton pants of the subject). Mean load at failure and percentage of diaper failed before 280 grams loading (termed as early leak) were used to represent diaper performance. Higher mean load and lower percentage of early leak indicate a better diaper performance. Table 4 summarizes results of the test.

TABLE 4

Forced Failure Test Results

| Superabsorbent | | Damage Level (Blending Time) | | |
|---|---|---|---|---|
| | | 0 seconds | 30 seconds | 60 seconds |
| SXM 9543[1] | Mean Load | 386 g | 367 g | 326 g |
| | % Early Leak | 6.2% | 14.4% | 29.0% |
| 2035[2] | Mean Load | 384 g | 342 g | |
| | % Early Leak | 9.8% | 24.0% | |

As can be seen in Table 4, the garments with superabsorbent materials subjected to minimum superabsorbent damage outperformed the other garments.

Example 5

In this Example, the damage resistance of a superabsorbent material was increased by introducing an aqueous solution of a hydrophilic soft polymer to the superabsorbent material to reduce the brittleness of the superabsorbent material. Suitable hydrophilic soft polymers have a glass transition temperature (Tg) at least below room temperature, or at least below 0 degrees Celsius.

In this Example, two hydrophilic soft polymers, 1:1 mole ratio acrylic acid:acrylate quaternary amine copolymer (Polymer A) and acrylate quaternary amine homopolymer (Polymer B), were used. Methods of making these polymers are listed below.

Preparation of Polymer A

Solution No. 1 was prepared as follows. To 14.4 grams (0.20 moles) of acrylic acid in a 200 ml beaker were added 6.0 grams of polyethylene glycol 200, followed by a solution of 3.2 grams of sodium hydroxide in 34 grams of distilled water. Then, 0.18 grams ($1.02 \times 10^{-3}$ moles) of ascorbic acid were added to the solution. This mixture was stirred with a magnetic stir bar at about 60 rpm in a bath of water at about 23 degrees Celsius until the ascorbic acid was dissolved and the mixture cooled to 23 degrees Celsius.

Solution No. 2 was prepared in the following manner. To 48.4 grams (0.20 moles) of 2-(acryloyloxy)ethyl-trimethylammonium chloride (80% solution in water), in a 300 ml beaker were added 6.0 grams of of polyethylene glycol 200, followed 0.37 ml of 30% aqueous hydrogen peroxide and 1.0 ml ($5.42 \times 10^{-3}$ moles) of 3-(trimethoxysilyl)propyl methacrylate. The ingredients were added with stirring to produce a clear solution. This mixture was stirred with a magnetic stir bar at about 60 rpm to provide a clear solution.

Solution No. 2 was added to Solution No. 1 while stirring with a magnetic stir bar at about 60 rpm. A thermocouple was used to monitor the temperature and observe the reaction exotherm. The polymerization reaction began within about 30 seconds of mixing as the temperature rose from 23 to 40 degrees Celsius. A maximum temperature of about 68 degrees Celsius was observed after three minutes of mixing the two solutions. An additional 40 grams of water was added to maintain a viscosity that could still be stirred by hand. The mixture was maintained in a water bath at 47 degrees Celsius for 70 minutes. The resulting polymer solution was diluted with 185 grams of water to form a uniform solution.

The resulting aqueous binder composition was cast into a crosslinked film by pouring 24.7 grams of solution into a polystyrene weigh boat with surface area of about 100 cm$^2$, and allowing the water to evaporate overnight in a hood at room temperature. The resulting film weighed 5.36 grams, indicating a solution concentration of about 22.1%.

The absorbent capacity of the film was tested using the Centrifuge Retention Capacity test described in the test method section. The film had an absorbent capacity of 12.2 g/g of its dry weight of the saline solution.

Preparation of Polymer B

Two monomer solutions were prepared separately. Solution No. 1 was prepared as follows. To 67.3 grams of an 80% solution of 2-(acryloyloxy)ethyl-trimethylammonium methyl sulfate (0.20 moles) were added 25.3 grams of deionized water, and 6.0 grams of PEG 200 (molecular weight 200). Then, 0.18 grams ($1.02 \times 10^{-3}$ moles) of ascorbic acid were added to the solution. This mixture was stirred with a magnetic stir bar at about 60 rpm in a bath of water at about 23 degrees Celsius until the ascorbic acid was dissolved.

Solution No. 2 was prepared in the following manner. To 67.3 grams of an 80% solution of 2-(acryloyloxy)ethyl-trimethylammonium methyl sulfate (0.20 moles) were added 25.3 grams of deionized water, and 6.0 grams of PEG 200 (molecular weight 200), 0.37 ml of 30% aqueous hydrogen peroxide and 1.0 ml ($5.42 \times 10^{-3}$ moles) of 3-(trimethoxysilyl)propyl methacrylate. This mixture was stirred with a magnetic stir bar at about 60 rpm in a bath of water at about 23 degrees Celsius to provide a clear solution.

Solution No. 2 was added to Solution No. 1 in a water bath at a temperature of 37 degrees Celsius. A thermocouple was used to monitor the temperature and observe the reaction exotherm. Within 3 minutes after the solutions were combined an exotherm was evident by a rise in temperature to 73 degrees Celsius over a period of 1 minute and the solution became highly viscous. The reaction beaker was removed from the water bath after 60 minutes from the addition of Solution No. 2 to Solution No. 1. Then, 150 grams of deionized water were added to reduce the polymer concentration to about 25%.

To 50 grams of the 25% polymer solution were added 2.5 ml of a 0.2% solution of hydrochloric acid. This solution was poured into two weighing dishes (100 cm$^2$ area) and the solution was dried for two days in the laboratory hood. The resultant film was very soft and flexible and slightly tacky. A portion of the film was cut off (0.5 gram) and soaked in 20 ml of 0.9% saline for 60 minutes. The absorbent capacity of the film was tested using the Centrifuge Retention Capacity test described in the Test Method section. The film swelled substantially and absorbed about 7.1 g/g of its dry weight of the saline solution.

Fifty (50) grams of a 10% solution of Polymer A was weighed and added into a 500 ml glass beaker. Into this beaker, 200 grams of distilled water were added and stirred for 5 minutes to form a uniform solution A1. In a similar manner, 84 grams of a 10% solution of Polymer A was weighed and added into a 500 ml glass beaker. Into this beaker, 336 grams of distilled water were added and stirred for 5 minutes to form a uniform solution A2. Also, 50 grams of a 10% solution of Polymer B were weighed and added into a 500 ml glass beaker. Into this beaker, 200 grams of distilled water were added and stirred for 5 minutes to form a uniform solution B. Then, 100 grams of SXM 9543 were added to each solution and stirred vigorously. The swollen superabsorbents were dried in an oven at 80 degrees Celsius overnight. The dried superabsorbents with hydrophilic soft polymer additives were screened through an 850 micron sieve and any particles larger than 850 microns were pressed by hand to separate any agglomerated particles. No mechanical force was used to ensure no occurrence of damage. Some of the dried and screened SXM 9543 particles were damaged by the blender for 30 seconds according to Absorbent Product Processing Simulation Test. The superabsorbents before being damaged by the blender were designated as the prepared samples, while those that were damaged were designated as the blend samples.

Since PSD and absorbency for the treated 9543 were no longer the same as those of the virgin material, the damaged treated 9543 (blend samples) was compared with the treated 9543 (as prepared). The results in Table 5 clearly show a trend wherein the addition of the hydrophilic soft polymers enhances resistance to mechanical damage. More particularly, this treatment significantly increases GBP values at all conditions of the prepared superabsorbents, and minimizes reduction in these GBP and average particle size through processing.

In this Comparative Example, a hydrophobic latex emulsion, AIRFLEX 192 available from Air Product & Chemical, Inc., was used. Various amounts (2.5, 5, and 10 weight percent based on dry superabsorbent) of AIRFLEX 192 were separately weighed and added into three 250 ml glass beakers. Into these three beakers, distilled water was added to 25 grams of total weight of AIRFLEX 192 and the added water, and stirred for 2 minutes to form a uniform emulsion. Ten (10) grams of SXM 9543 were added into each diluted emulsion and stirred vigorously. The swollen superabsorbents were dried in an oven at 60 degrees Celsius overnight. The dried superabsorbents with hydrophobic soft polymer additives were screened through an 850 micron sieve and any particles larger than 850 microns were pressed by hand to separate agglomerated particles. No mechanical force was used to ensure no occurrence of damage. The dried and screened SXM 9543 particles were damaged by the blender for 30 seconds.

Since PSD and absorbency for the treated 9543 were no longer the same as those of the virgin material, the damaged treated 9543 was compared with the original treated 9543 (as prepared). The results in Table 6 clearly show a trend wherein the addition of AIRFLEX 192 enhances resistance to mechanical damage. However, the addition also signifi-

TABLE 5

Damage Resistant Superabsorbents by Hydrophilic Soft Polymers

| Property | SXM 9543[4] Virgin | SXM 9543[4] Blend | 9543[4] & 5% Polymer A Prep | 9543[4] & 5% Polymer A Blend | 9543[4] & 8.4% Polymer A Prep | 9543[4] & 8.4% Polymer A Blend | 9543[4] & 5% Polymer B Prep | 9543[4] & 5% Polymer B Blend |
|---|---|---|---|---|---|---|---|---|
| CRC (g/g) | 21.2 | 22.5 | 18.3 | 20.5 | 17.5 | 19.1 | 17.5 | 19.3 |
| 0.9 AUL (g/g) | 20.1 | 19.5 | 16.8 | 16.8 | 15.7 | 16.3 | 16.2 | 16.8 |
| GBP @ 0 psi on 300–600 micron particles ($\times 10^{-9}$ cm$^2$) | 241.7 | 154.7 | 533 | 453 | 508 | 505 | 1135 | 778 |
| Reduction in GBP @ 0 psi | | −36.0% | | −15.0% | | −0.6% | | −31.5% |
| GBP @ 0.3 psi on 300–600 micron particles ($\times 10^{-9}$ cm$^2$) | 67.3 | 5.0 | 205 | 178 | 267 | 179 | 310 | 234 |
| Reduction to GBP @ 0.3 psi | | −92.6% | | −13.2% | | −33.0% | | −24.5% |
| GBP @ 0 psi on as-is particles ($\times 10^{-9}$ cm$^2$) | 89 | 41 | 401 | 199 | 611 | 231 | 963 | 326 |
| Reduction to GBP@ 0 psi | | −53.9% | | −50.4% | | −62.2% | | −66.1% |
| GBP @ 0.3 psi on as-is particles ($\times 10^{-9}$ cm$^2$) | 32 | 1.0 | 187 | 102 | 265 | 130 | 227 | 146 |
| Reduction to GBP @ 0.3 psi | | −96.9% | | −45.5% | | −50.9% | | −35.7% |
| Average PSD (μm) | 357.2 | 257.9 | 463.1 | 371.3 | 481.5 | 306.7 | 445.5 | 304.8 |
| Reduction to average PSD | | −27.8% | | −19.8% | | −36.3% | | −31.6% |

Comparative Example to Example 5

In this Comparative Example, the damage resistance of a superabsorbent material was increased by introducing an emulsion of a hydrophobic soft polymer to the superabsorbent material to reduce the brittleness of the superabsorbent material. Suitable hydrophobic soft polymers have a glass transition temperature (Tg) at least below room temperature.

cantly reduces GBP values at all conditions of the prepared samples. For example, when 2.5%, 5% or 10% AIRFLEX 192 was added onto SXM 9543, the treated SXM 9543 had a GBP @ 0 psi value reduced from $241.7 \times 10^{-9}$ cm$^2$ to $131.3 \times 10^{-9}$ cm$^2$, $98.2 \times 10^{-9}$ cm$^2$, and $85.9 \times 10^{-9}$ cm$^2$, respectively. The GBP values of the prepared SXM 9543 before mechanical damage are outside of this invention. It is desirable to have a GBP @ 0 psi value of about $200 \times 10^{-9}$ cm$^2$ or greater.

TABLE 6

Damage Resistant Superabsorbents by Hydrophobic Soft Additives

| Property | SXM 9543[4] Virgin | SXM 9543[4] Blend | 9543[4] & 2.5% AIRFLEX Prep | 9543[4] & 2.5% AIRFLEX Blend | 9543[4] & 5% AIRFLEX Prep | 9543[4] & 5% AIRFLEX Blend | 9543[4] & 10% AIRFLEX Prep | 9543[4] & 10% AIRFLEX Blend |
|---|---|---|---|---|---|---|---|---|
| CRC (g/g) | 21.2 | 22.5 | 19.7 | 20.3 | 18.6 | 19.8 | 17.3 | 18.6 |
| 0.9 AUL (g/g) | 20.1 | 19.5 | 17.8 | 18.2 | 17.1 | 18.0 | 15.9 | 17.1 |
| GBP @ 0 psi on 300–600 micron particles ($\times 10^{-9}$ cm$^2$) | 241.7 | 154.7 | 131.3 | 106.6 | 98.2 | 102.9 | 85.9 | 99.8 |
| Reduction in GBP @ 0 psi | | −36.0% | | −18.8% | | 4.8% | | 16.2% |
| GBP @ 0.3 psi on 300–600 micron particles ($\times 10^{-9}$ cm$^2$) | 67.3 | 5.0 | 60.7 | 54.0 | 63.5 | 50.9 | 37.6 | 44.9 |
| Reduction in GBP @ 0.3 psi | | −92.6% | | −11.0% | | −19.8% | | 19.4% |
| GBP @ 0 psi on as-is particles ($\times 10^{-9}$ cm$^2$) | 89 | 41 | 56 | 45 | 43 | 36 | 39 | 32 |
| Reduction in GBP @ 0 psi | | −53.9% | | −19.6% | | −16.3% | | −17.9% |
| GBP @ 0.3 psi on as-is particles ($\times 10^{-9}$ cm$^2$) | 32 | 1.0 | 25 | 18 | 23 | 20 | 14 | 16 |
| Reduction in GBP @ 0.3 psi | | −96.9 | | −28.0% | | −13.0% | | 14.3% |
| Average PSD (μm) | 357.2 | 257.9 | 352.8 | 303.5 | 344.3 | 319.9 | 349.1 | 348.4 |
| Reduction in average PSD | | −27.8% | | −14.0% | | −7.10% | | −0.22% |

Test Methods

Figure 2:
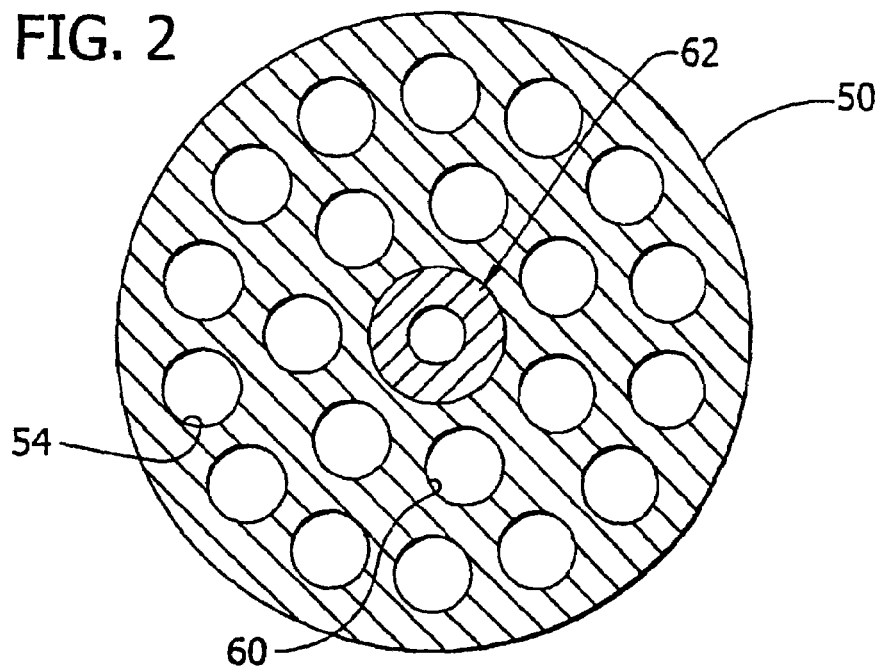
FIG. 2 depicts a bottom view of the apparatus of FIG. 1.

Gel Bed Permeability (GBP) @ 0 psi Swell Pressure Test:

As used herein, the Gel Bed Permeability (GBP) @ 0 psi swell pressure test determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1 and 2 and indicated generally at 28. The test apparatus 28 comprises a sample container, generally indicated at 30, and a piston, generally indicated at 36. The piston 36 comprises a cylindrical LEXAN shaft 38 having a concentric cylindrical hole 40 bored down the longitudinal axis of the shaft. Both ends of the shaft 38 are machined to provide upper and lower ends respectively designated 42, 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 100 mesh stainless steel screen 64.

The sample container 30 comprises a cylinder 34 and a 400 mesh stainless steel cloth screen 66 that is biaxially stretched to tautness and attached to the lower end of the cylinder. A gel particle sample, indicated as 68 in FIG. 1, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 10 cm. Drainage holes (not shown) are formed in the sidewall of the cylinder 34 at a height of approximately 7.8 cm above the screen 66 to allow liquid to drain from the cylinder to thereby maintain a fluid level in the sample container at approximately 7.8 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is 0.9 weight percent sodium chloride solution in distilled water. The combined weight of the piston 36 and annular weight 48 equals approximately 596 grams (g), which corresponds to a pressure applied to the sample 68 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Gel Bed Permeability Test under "free swell" conditions, the piston 36, with the weight 48 seated thereon, is placed in an empty sample container 30 and the height is measured using a suitable gauge accurate to 0.01 mm with the platen removed. It is important to measure the height of each sample container 30 empty and to keep track of which piston 36 and weight 48 is used when using multiple test apparatus. The same piston 36 and weight 48 should be used for measurement when the sample 68 is later swollen following saturation.

The sample to be tested is prepared from particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Also test samples can be as-is particles. Approximately 0.9 grams of the sample is placed in the sample container 30 and spread out evenly on the bottom of the sample container. The container, with 0.9 grams of sample in it, without the piston 36 and weight 48 therein, is then submerged in the test solution for a time period of about 60 minutes to saturate the sample and allow the sample to swell free of any restraining load.

At the end of this period, the piston 36 and weight 48 assembly is placed on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same thickness gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of test solution into the container is adjusted to maintain a fluid height of about 7.8 cm above the bottom of the sample container. The quantity of solution passing through the sample 68 versus time is measured gravimetrically. Data points are collected every second for at least twenty seconds once the fluid level has been stabilized to and maintained at about 7.8 cm in height. The flow rate Q through the swollen sample 68 is determined in units of grams/second (g/s) by a linear least-square fit of fluid passing through the sample 68 (in grams) versus time (in seconds).

Permeability in cm$^2$ is obtained by the following equation:

$$K=[Q*H*\mu]/[A*\rho*P]$$

where K=Permeability (cm$^2$), Q=flow rate (g/sec), H=height of sample (cm), μ=liquid viscosity (poise) (approximately one centipoises for the test solution used with this Test), A=cross-sectional area for liquid flow (cm$^2$), ρ=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P=\rho*g*h$$

where ρ=liquid density (g/cm$^3$), g=gravitational acceleration, nominally 981 cm/sec$^2$, and h=fluid height, e.g., 7.8 cm for the Gel Bed Permeability Test described herein.

A minimum of three samples is tested and the results are averaged to determine the gel bed permeability of the sample.

GBP @ 0.3 psi Swell Pressure Test:

As used herein, the Gel Bed Permeability (GBP) Under Load Test, otherwise referred to herein as GBP at 0.3 psi, determines the permeability of a swollen bed of gel particles (e.g., the superabsorbent material or the absorbent material as those terms are used herein), under conditions that are commonly referred to as being "under load" conditions. The term "under load" means that swelling of the particles is restrained by a load generally consistent with normal usage loads applied to the particles, such as sitting, walking, twisting, etc. by the wearer.

More particularly, the Gel Bed Permeability Under Load Test is substantially the same as the Free Swell Gel Bed Permeability Test set forth previously with the following exception. After approximately 0.9 grams of the sample is placed in the sample container 30 and spread out evenly on the bottom of the sample container, the piston 36 and weight 48 are placed on the sample within the sample container prior to the sample container (with the piston and weight therein) being submerged in the test solution (0.9 wt % NaCl saline) for a time period of about 60 minutes. As a result, a 0.3 psi restraining load is applied to the sample as the sample becomes saturated and swells.

Average Particle Size Distribution Test

The PSD test method used in the present invention determines the particle size distribution of a superabsorbent material by sieve size analysis. A stack of sieves with different size openings are used to determine the particle size distribution of a given sample. Thus, for example, in principle, a particle that is retained on a sieve with 600 micron openings is considered to have a particle size greater than 600 microns. A particle that passes through a sieve having 600 micron openings and is retained on a sieve having 300 micron openings is considered to have a particle size between 300 and 600 microns. Further, a particle that passes through a sieve having 300 micron openings is considered to have a particle size less than 300 microns.

The sieves having 850, 600, 300, 90 and 45 microns openings are placed in order of the size of the openings with the largest openings on the top of the stack and the smallest openings on the bottom of the stack. The stack is placed on the top of a pan. A 25 gram sample of superabsorbent particles is placed into the sieve with the largest openings. The sieve stack is shook for 10 minutes with a Ro-Tap Mechanical Sieve Shaker, Model B. available from W.S. Tyler of Mentor, Ohio, or other similar shaking device. After shaking is complete, the superabsorbent particles retained on each sieve are removed and the weight is measured and recorded. The percentage of particles retained on each sieve is calculated by dividing the weights of the particles retained on each sieve by the initial sample weight. A minimum of four samples is tested and the results are averaged to determine the percentage of particles retained on each sieve of the sample. Average particle size diameter (PSD) is calculated by the following equation:

$$\text{Average } PSD = \frac{850 W_{850} + 600 W_{600} + 300 W_{300} + 90 W_{90} + 45 W_{45} + W_{pan}}{100}$$

Wherein W represents average weight percentage of particles retained on each sieve and footnote represents opening size of each sieve.

Centrifuge Retention Capacity

The Centrifuge Retention Capacity (CRC) Test measures the ability of the gel particles (e.g., such as the surface treated absorbent material or the superabsorbent material prior to being surface treated) to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed (W), with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{W_{(sample+bag) after-centrifuge} - W_{(bag) after-centrifuge} - W_{dry-sample}}{W_{dry-sample}}$$

The three samples are tested and the results are averaged to determine the centrifuge retention capacity (CRC). The samples are tested at 23±1 degrees Celsius at 50±2 percent relative humidity.

Absorbency Under Load (AUL @ 0.9 psi) Test

Figure 3:
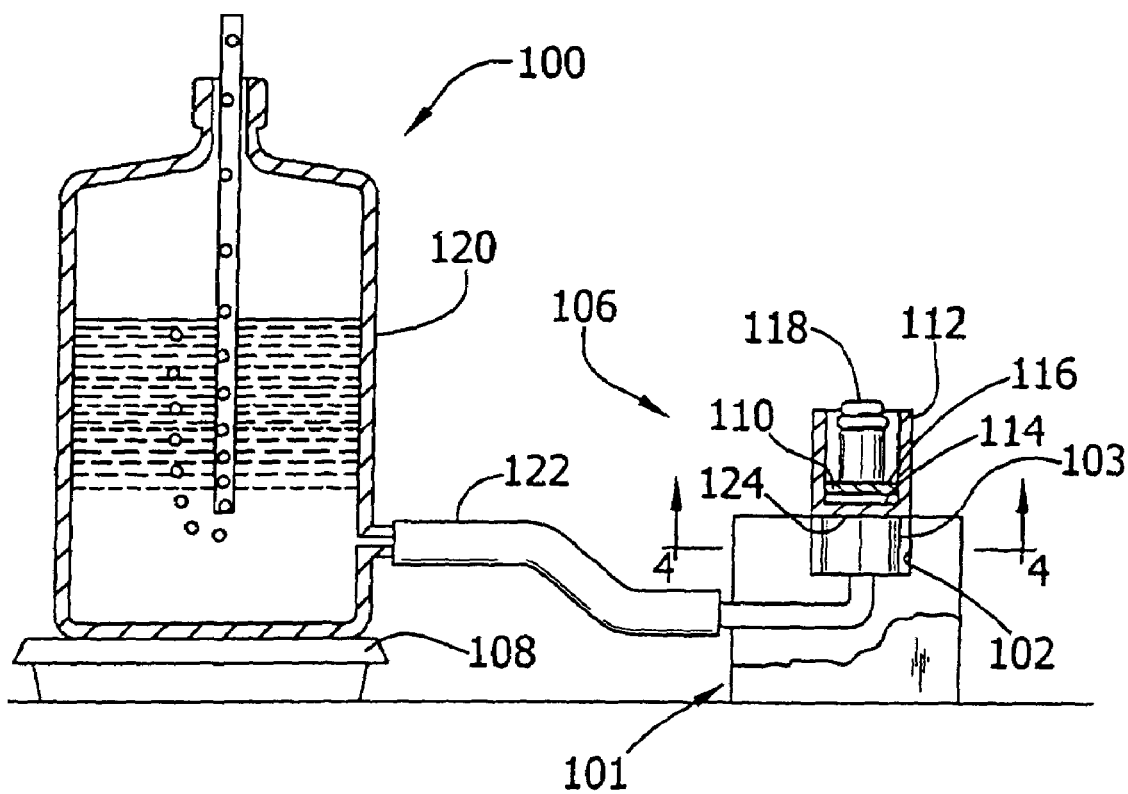
FIG. 3 depicts apparatus used to measure absorbency under load (AUL) of free-flowing particles.

The Absorbency Under Load (AUL) Test measures the ability of the gel particle sample (e.g., such as the surface treated absorbent material or the superabsorbent material prior to being surface treated) to absorb a 0.9 weight percent solution of sodium chloride in distilled water at room temperature (test solution) while the material is under a 0.9 psi load. Apparatus 106 for conducting the AUL Test is shown in FIG. 3 and comprises a Demand Absorbency Tester (DAT), generally indicated at 100, which is similar to the Gravimetric Absorbency Test System (GATS) available from M/K Systems of Danners, Mass., U.S.A., and to the system described by Lichstein at pages 129–142 of the INDA Technological Symposium Proceedings, March 1974.

Figure 4:
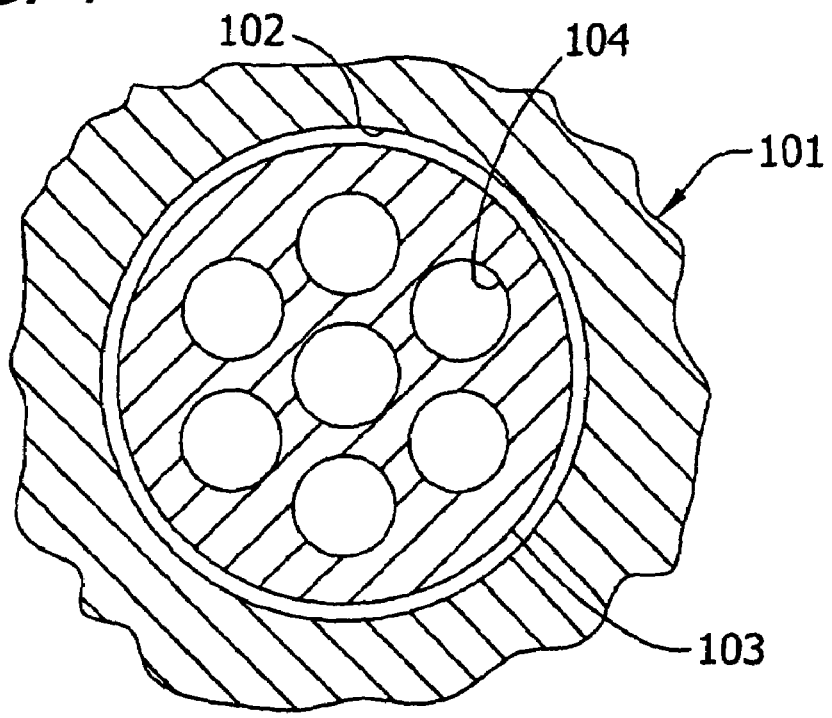
FIG. 4 depicts a bottom view of the apparatus of FIG. 3.

The test apparatus further comprises a test stand, generally indicated at 101 (FIG. 4) having a cavity 102 formed therein and a porous plate 103 seated in the cavity and having a central porous area of about 2.54 cm diameter formed by a plurality of bores 104 extending through the plate. The cavity 102 shown in FIG. 4 has a diameter of about 3.2 cm and the porous plate 103 has a diameter of about 3.1 cm and comprises seven bores 104, each having a diameter of about 0.3 cm. One of the bores 104 is centrally located and the remaining six bores are concentrically positioned about the central bore with the spacing from the center of the central bore to the center of each adjacent bore is about one centimeter.

A sample container for containing a sample 110 to be tested includes a cylinder 112 and a stainless steel cloth screen 114 that is biaxially stretched to tautness and attached to the lower end of the cylinder. The cylinder 112 may be bored from a transparent LEXAN rod or equivalent material, or it may be cut from a LEXAN tubing or equivalent material, and has an inner diameter of about one inch (about 2.54 cm). The stainless steel cloth screen 114 is suitably a 100 mesh screen A disc, or piston 116 is machined from a LEXAN rod, Plexiglass or equivalent material and has a diameter sized such that it fits within the cylinder 112 with minimum wall clearance but still slides freely. The height of the piston 116 is approximately 0.8 cm and the weight of the piston is suitably about 4.4 grams to provide a load over the cross-sectional area of the sample in the container of about 0.01 psi. A weight 118 is sized (e.g., having a diameter of about 2.5 cm) for seating on the piston 116 to increase the load (e.g., in addition to the weight of the piston) on the sample. For example, a weight of about 317 grams is used to provide a load (e.g., including the piston weight) of about 0.9 psi over the cross-sectional area of the sample in the container.

The cavity 102, and hence the porous plate 103, is in fluid communication with a reservoir 120 containing test solution (0.9 weight percent sodium chloride solution in distilled water at room temperature) via a suitable conduit 122. As shown in FIG. 3, the reservoir 120 is seated on an electrostatic balance 108.

A sample 110 of gel particles weighing about 0.160 grams is prepared by screening the particles through a U.S. standard 30 mesh screen and retaining the particles on a U.S. standard 50 mesh screen so that the sample comprises particles in the size range of about 300 to about 600 microns. The sample is weighed on suitable weighing paper and then loaded into the sample container (with the piston 116 removed) so that the particles are uniformly distributed and uniformly distributed and overlay the screen at the bottom of the container. The sample container is gently tapped to level the bed of particles in the container.

The AUL Test is initiated by placing a circular piece of GF/A glass filter paper 124 into the porous plate 103 over the bores 104 formed therein and allowing to become saturated by test solution delivered from the reservoir 120 to the porous plate via the conduit 122. The paper 124 is suitably sized larger than the inner diameter of the cylinder 112 and smaller than the outer diameter thereof to ensure good contact while inhibiting evaporation over the bores 104. The electrostatic balance 108 is zeroed at this time. The piston 116 and weight 118 are placed on the sample within the container and the container (with the sample, piston and weight therein) is placed on the plate 103 over the saturated glass filter paper 124 to allow test solution to be taken into the sample in the container via the conduit 122, bores 104 in the plate 102 and the filter paper.

The electrostatic balance 108 is used to measure the flow of test solution to the sample over a period of about 60 minutes. The amount (in grams) of solution taken into the sample after about 60 minutes divided by the dry weight of the sample (e.g., about 0.160 grams) is the AUL value of the sample in grams of liquid per gram weight of sample.

Two checks can be made to ensure the accuracy of the measurement. First, the height the piston 116 rises above the screen 114 at the bottom of the sample container multiplied by the cross-sectional area of the piston should roughly equal the amount of solution picked up by the sample over the 60 minute period. Second, the sample container can be weighed before (e.g., while the superabsorbent material is dry) and after the test and the difference in weight should roughly equal the amount of solution picked up by the sample over the 60 minute period.

A minimum of three tests is performed and the results are averaged to determine the AUL value at 0.9 psi. The samples are tested at 23±1 degrees Celsius at 50±2 percent relative humidity.

Absorbent Product Processing Simulation Test

Place 50 grams of superabsorbent material in an OSTERIZER® 12-speed blender, available from Sunbeam Products, Inc., of Boca Raton, Fla. Blend the superabsorbent material for 30 seconds with the blender set on "high speed" and "blend."

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A superabsorbent material, comprising:
    a superabsorbent material treated with a coating including a hydrophilic soft polymer crosslinked with an acrylate or methacrylate ester having an alkoxysilane functionality to resist damage when subjected to an Absorbent Product Processing Simulation Test;
    wherein the treated superabsorbent material has a centrifuge retention capacity of about 15 grams or greater of 0.9 weight percent sodium chloride aqueous solution per gram of the treated superabsorbent material and a gel bed permeability (GBP) at a 0 psi swell pressure on pre-screened 300–600 micron particles of about 200 ($\times 10^{-9}$ cm$^2$) or greater prior to subjecting the treated superabsorbent material to the Absorbent Product Processing Simulation Test; and subsequent to subjecting the treated superabsorbent material to the Absorbent Product Processing Simulation Test the treated superabsorbent material exhibits at least one property selected from the group consisting of: (1) a reduction in GBP value at a 0 psi swell pressure on pre-screened particles of about 20% or less; (2) a reduction in GBP value at a 0.3 psi swell pressure on pre-screened particles of about 50% or less; (3) a reduction in GBP value at a 0 psi swell pressure on un-screened particles of about 50% or less; (4) a reduction in GBP value at a 0.3 psi swell pressure on un-screened particles of about 60% or less; and (5) an average particle size reduction of about 20% or less.

2. The superabsorbent material of claim 1, wherein the superabsorbent material is treated with about 10% to about 1000% aqueous solution of the hydrophilic soft polymer by weight of the superabsorbent material, wherein the hydrophilic soft polymer has a glass transition temperature of about 20 degrees Celsius or less.

3. The superabsorbent material of claim 1, wherein the treated superabsorbent material has a GBP value at a 0 psi swell pressure on pre-screened 300–600 micron particles of about 800 ($\times 10^{-9}$ cm$^2$) or greater prior to subjecting the treated superabsorbent material to the Absorbent Product Processing Simulation Test.

4. The superabsorbent material of claim 1, wherein the treated superabsorbent material has a centrifuge retention capacity of about 20 grams or greater of 0.9 weight percent sodium chloride aqueous solution per gram of the treated superabsorbent material prior to subjecting the treated superabsorbent material to the Absorbent Product Processing Simulation Test.

5. The superabsorbent material of claim 1, wherein the treated superabsorbent material has a centrifuge retention capacity of about 25 grams or greater of 0.9 weight percent sodium chloride aqueous solution per gram of the treated superabsorbent material prior to subjecting the treated superabsorbent material to the Absorbent Product Processing Simulation Test.

6. The superabsorbent material of claim 1, wherein, subsequent to subjecting the treated superabsorbent material to the Absorbent Product Processing Simulation Test, the treated superabsorbent material exhibits at least two properties selected from the group consisting of: (1) a reduction in GBP value at a 0 psi swell pressure on pre-screened particles of about 20% or less; (2) a reduction in GBP value at a 0.3 psi swell pressure on pre-screened particles of about 50% or less; (3) a reduction in GBP value at a 0 psi swell pressure on un-screened particles of about 50% or less; (4) a reduction in GBP value at a 0.3 psi swell pressure on on-screened particles of about 60% or less; and (5) an average particle size reduction of about 20% or less.

7. The superabsorbent material of claim 1, wherein, subsequent to subjecting the treated superabsorbent material to the Absorbent Product Processing Simulation Test, the treated superabsorbent material exhibits at least three properties selected from the group consisting of: (1) a reduction in GBP value at a 0 psi swell pressure on pre-screened particles of about 20% or less; (2) a reduction in GBP value at a 0.3 psi swell pressure on pre-screened particles of about 50% or less; (3) a reduction in GBP value at a 0 psi swell pressure on un-screened particles of about 50% or less; (4) a reduction in GBP value at a 0.3 psi swell pressure on un-screened particles of about 60% or less; and (5) an average particle size reduction of about 20% or less.

8. The superabsorbent material of claim 1, wherein, subsequent to subjecting the treated superabsorbent material to the Absorbent Product Processing Simulation Test, the treated superabsorbent material exhibits at least four properties selected from the group consisting of: (1) a reduction in GBP value at a 0 psi swell pressure on pre-screened particles of about 20% or less; (2) a reduction in GBP value at a 0.3 psi swell pressure on pre-screened particles of about 50% or less; (3) a reduction in GBP value at a 0 psi swell pressure on un-screened particles of about 50% or less; (4) a reduction in GBP value at a 0.3 psi swell pressure on un-screened particles of about 60% or less; and (5) an average particle size reduction of about 20% or less.

9. The superabsorbent material of claim 1, wherein the treated superabsorbent material has a GBP value at a 0.3 psi swell pressure on pre-screened 300–600 micron particles of about 100 ($\times 10^{-9}$ cm$^2$) or greater, and a centrifuge retention capacity of about 25 grams or greater of 0.9 weight percent sodium chloride aqueous solution per gram of the treated superabsorbent material, prior to subjecting the treated superabsorbent material to the Absorbent Product Processing Simulation Test.

10. The superabsorbent material of claim 1, wherein the treated superabsorbent material has a GBP value at a 0.3 psi swell pressure on pre-screened 300–600 micron particles of about 200 ($\times 10^{-9}$ cm$^2$) or greater, and a centrifuge retention capacity of about 25 grams or greater of 0.9 weight percent sodium chloride aqueous solution per gram of the treated superabsorbent material, prior to subjecting the treated superabsorbent material to the Absorbent Product Processing Simulation Test.

11. The superabsorbent material of claim 1, wherein, subsequent to subjecting the treated superabsorbent material to the Absorbent Product Processing Simulation Test, the treated superabsorbent material exhibits a reduction in GBP value at 0 psi swell pressure on pre-screened 300–600 micron particles of about 10% or less.

12. The superabsorbent material of claim 1, wherein, subsequent to subjecting the treated superabsorbent material to the Absorbent Product Processing Simulation Test, the treated superabsorbent material exhibits a reduction in GBP value at 0.3 psi &well pressure on pre-screened 300–600 micron particles of about 30% or less.

13. The superabsorbent material of claim 1, wherein, subsequent to subjecting the treated superabsorbent material to the Absorbent Product Processing Simulation Test, the treated superabsorbent material exhibits a reduction in GBP value at 0.3 psi swell pressure on un-screened particles of about 40% or less.

14. The superabsorbent material of claim 1, wherein the superabsorbent material comprises a crosslinked polyelectrolyte including at least one of the group consisting of anionic polymers, cationic polymers, and combinations thereof.

15. The superabsorbent material of claim 14, wherein the anionic polymers comprise functional groups selected from the group consisting of carboxyl, sulfonate, sulphate, sulfite, phosphate, and combinations thereof.

16. The superabsorbent material of claim 14, wherein the anionic polymers are selected from the group consisting of salts of polyacrylic acid, polyacrylamido methylpropane sulfonic acid, polyvinyl acetic acid, polyvinyl phosphonic acid, polyvinyl sulfonic acid, isobutylene-maleic anhydride copolymer, carboxymethyl cellulose, alginic acid, carrageenan, polyaspartic acid, polyglutamic acid, and copolymers or mixtures thereof.

17. The superabsorbent material of claim 14, wherein the cationic polymers comprise functional groups selected from the group consisting of primary, secondary, and tertiary amine, imine, amide, quaternary ammonium, and combinations thereof.

18. The superabsorbent material of claim 14, wherein the cationic polymers are selected from the group consisting of salts of polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine, and copolymers or mixtures thereof.

19. An absorbent material comprising the superabsorbent material of claim 1.

20. An absorbent article comprising the superabsorbent material of claim 1.

21. The absorbent article of claim 20, comprising an absorbent layer having at least one region containing superabsorbent material in a concentration of about 10% superabsorbent material or greater based on total weight of the absorbent layer.

22. The superabsarbent material of claim 1, wherein the hydrophilic soft polymer has a glass transition temperature of about 20° C. or less.

23. The superabsorbent material of claim 22, wherein the hydrophilic soft polymer has a glass transition temperature of about 0° C. or less.

24. The superabsorbent material of claim 22, wherein the hydrophilic soft polymer further comprises at least one of the group consisting of hydroxypropyl cellulose, polyethylene oxide, polypropylene oxide, polyethylene glycol, polypropylene glycol, hydrophilic acrylate copolymers, hydrophilic methacrylate copolymers, and combinations thereof.

25. The superabsorbent material of claim 22, wherein the hydrophilic soft polymer further comprises a reaction product of a monoethylenically unsaturated polymer and an acrylate or methacrylate ester.

26. The superabsorbent material of claim 22, wherein the hydrophilic soft polymer further comprises a reaction product of two different monoethylenically unsaturated monomers, one of which includes an alkoxysilane functionality.

27. The superabsorbent material of claim 22, wherein the hydrophilic soft polymer exhibits latent, moisture-induced crosslinking.

28. The superabsorbent material of claim 25, wherein the hydrophilic soft polymer further comprises a reaction product of the monoetbylenically unsaturated polymer, the acrylate or methacrylate ester, and a polyolefin glycol or oxide.

* * * * *